United States Patent [19] [11] 4,316,463
Schmitz et al. [45] Feb. 23, 1982

[54] CORROSIVE PROTECTED HYPODERMIC MODULE

[75] Inventors: William L. Schmitz, Hemet; John B. Schmitz, Arcadia, both of Calif.

[73] Assignee: Vac-O-Cast, Inc., Hemet, Calif.

[21] Appl. No.: 228,628

[22] Filed: Jan. 26, 1981

[51] Int. Cl.³ .............................................. A61M 5/20
[52] U.S. Cl. .................................................. 128/218 F
[58] Field of Search ................... 128/213, 215, 218 R, 128/218 F, 218 A, 218 D, 218 DA, 220, 234

[56] References Cited
U.S. PATENT DOCUMENTS

| | | | |
|---|---|---|---|
| 2,866,458 | 12/1958 | Hein, Jr. | 128/218 F |
| 3,066,670 | 12/1962 | Stauffer | 128/218 F |
| 3,136,313 | 6/1964 | Enstrom et al. | 128/218 F |
| 3,330,279 | 7/1967 | Sarnoff et al. | 128/218 F |
| 3,403,679 | 10/1968 | Sinclair et al. | 128/218 F |
| 4,194,505 | 3/1980 | Schmitz | 128/218 D |

Primary Examiner—John D. Yasko
Attorney, Agent, or Firm—Allan D. Mockabee

[57] ABSTRACT

A hypodermic injection device including an injector and a medicament and needle ampule wherein the needle is initially isolated from a possibly corrosive medicament, but wherein the needle is movable to a position in flow communication with the medicament only at the moment of injection, and an injector device into which the ampule can be loaded under controlled conditions of needle entry force and depth, medicament entry into tissue being accomplished while the needle is moving in its penetration of tissue.

18 Claims, 8 Drawing Figures

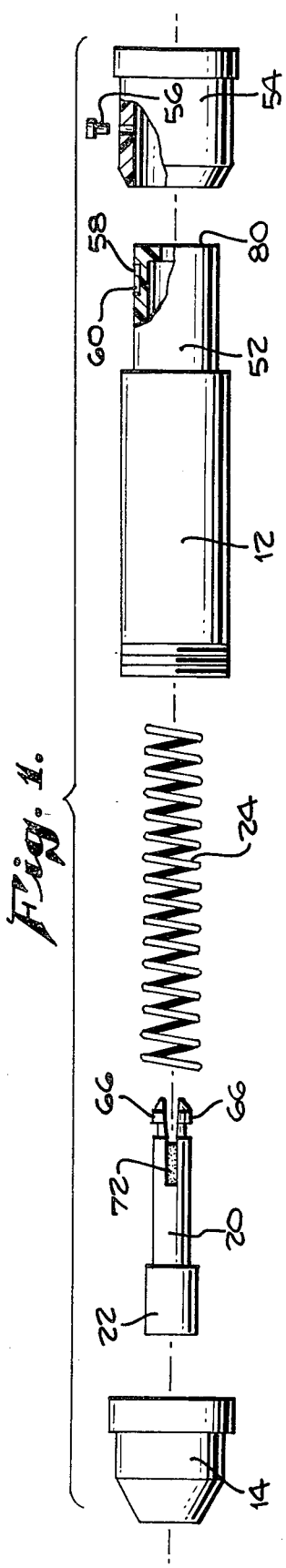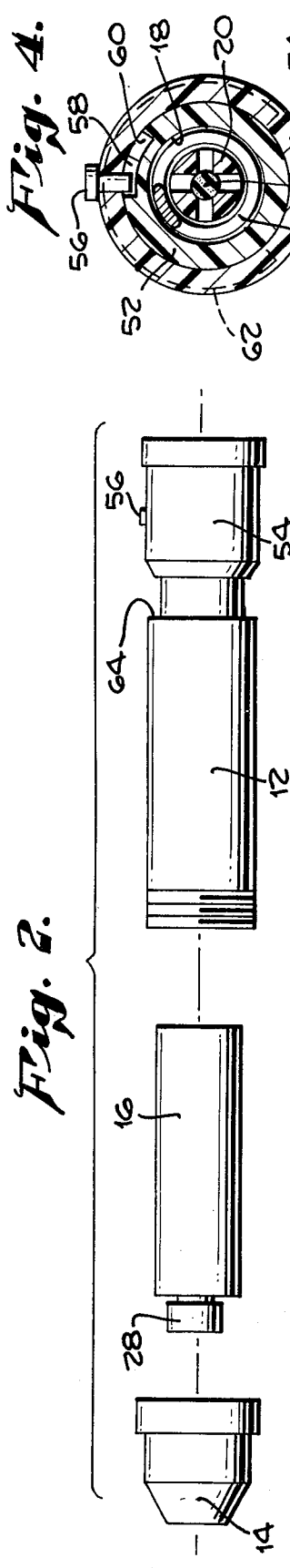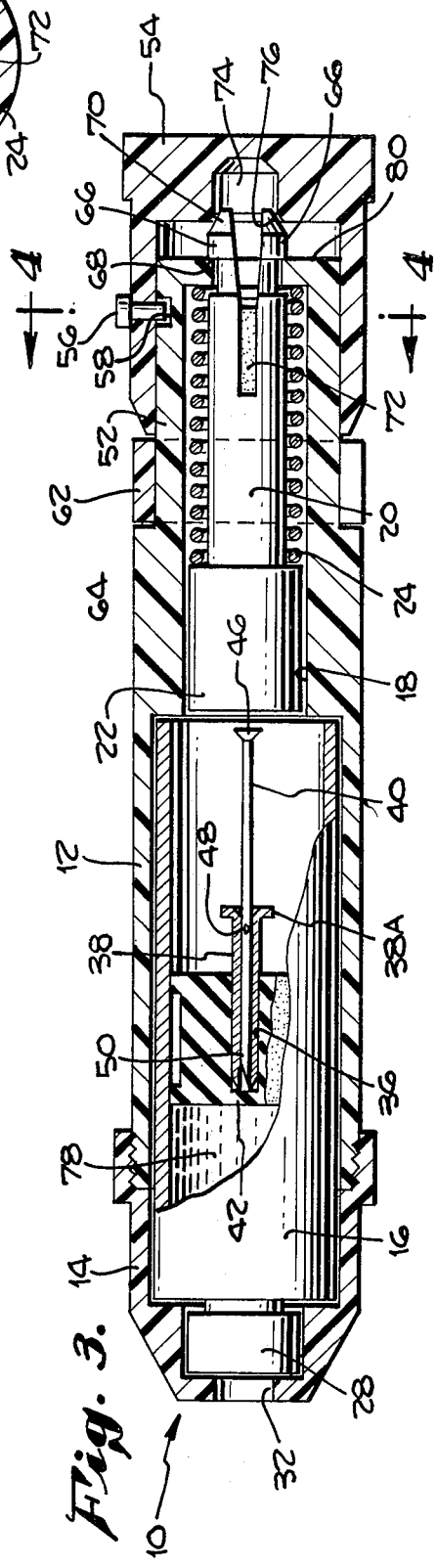

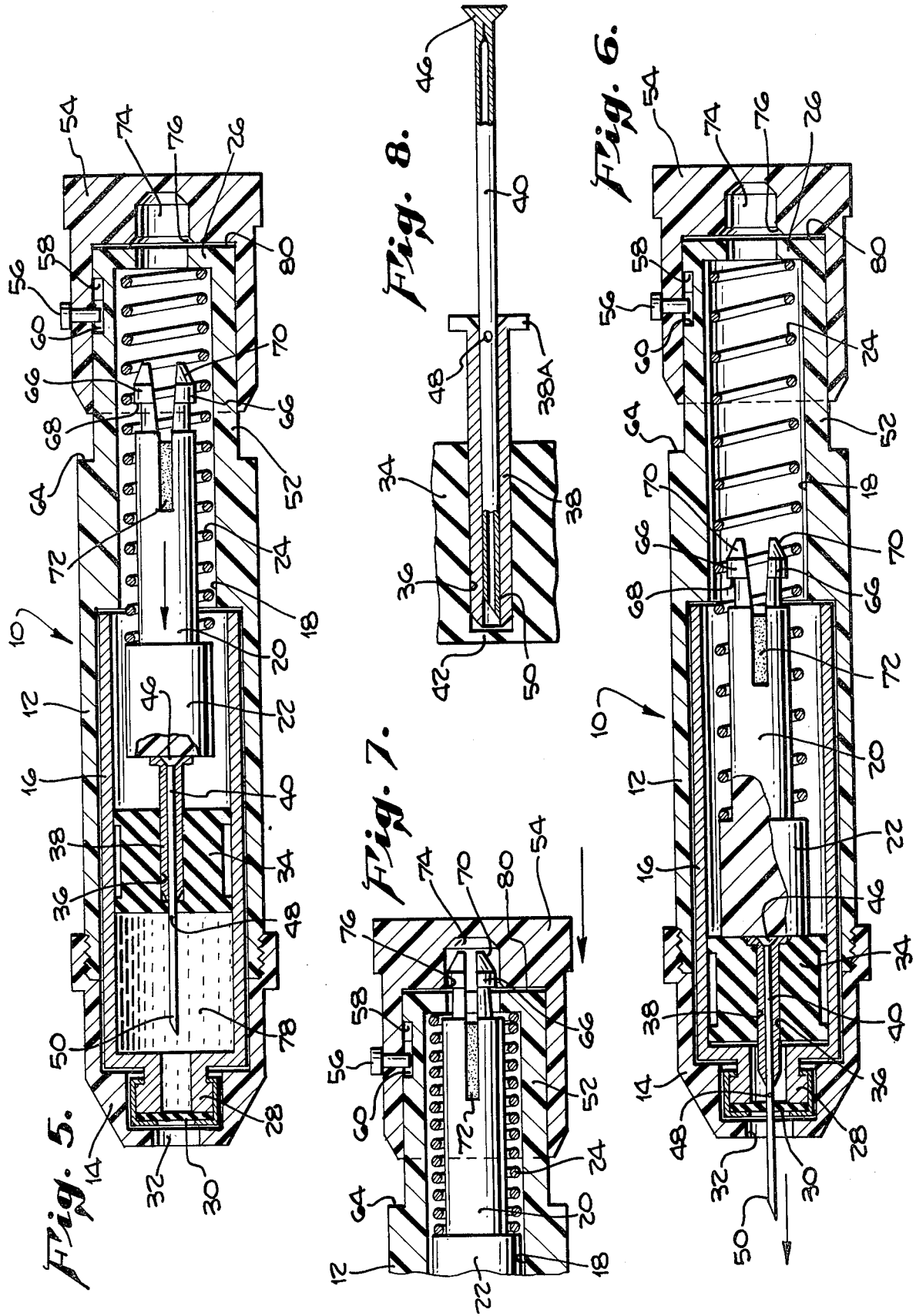

CORROSIVE PROTECTED HYPODERMIC MODULE

This invention relates to a hypodermic module including an ampule containing a medicament and a needle and an injector therefore, primarily for self-administration of measured doses of desired medicaments.

FIELD OF INVENTION

The invention is in the field of self-contained hypodermic modules and is particularly useful for the self-administration of pre-packaged dosages, as by military personnel for the injection of antidotes for poisonous gases, or by civilians for self-injection for various circumstances.

PRIOR ART

While there are numerous devices for self-administration of liquid medicines, the closest known to us are U.S. patents:
U.S. Pat. No. 3,136,313, Enstrom, June 9, 1964
U.S. Pat. No. 4,194,505, Schmitz, Mar. 25, 1980

The Schmitz patent shows a device wherein there is an ampule to contain the medicament and to support the needle which is submerged in the medicament until such time as it is put to use. It has an injector mechanism, but in the instant invention the injector is more compact and does not have the projecting trigger structure and it does not have a rearwardly projecting plunger reset rod as in the patent.

The patent to Enstrom discloses a device wherein the medicament and the needle are sealed from each other until use to prevent corrosion of the needle with some types of corrosive liquids. In that patent the needle is held in the injector housing in front of the medicament ampule and both the front and rear ends of the needle must pierce diaphragms or seals which lie respectively in front of the front end and at the rear of the rear end of the needle. Patentee Enstrom states in column 2, lines 42 through 50, "At first the rod 14 pushes the whole cartridge type ampoule 4 forwards so that the perforator 7 pierces the front wall 8 of the ampoule, thereafter the ampoule phases the needle holder 3 and the needle 2 forwards so that the needle pierces the rubber membrane 9 and is brought into position for injecting. Thereupon the piston rod 14 pushes the piston 11 into the cartridge type ampoule, causing the injection fluid to be forced out through the needle 2."

It is apparent from the Enstrom disclosure that his needle is projected fully from his syringe or injector and that the needle has penetrated to its greatest depth in the tissue of the patient before the seal at the rear end of the needle is pierced and the medicament is forced through the needle and into the tissue where the injection is concentrated in a small area and causing considerable instant and residual pain. However, with the present invention, not only is the needle isolated from the liquid medicament until the injector is actuated but the structure and operation are such that liquid is forced through and from the needle from the time the skin is pierced until the needle has completed its prescribed depth of penetration of the tissue. At such point all or a large percentage of the medicament has already been injected and the possibility of painful tissue rupturing is greatly if not entirely minimized.

DISCLOSURE

The above and other objects of the invention will more fully appear from the following description in connection with the accompanying drawing.

FIG. 1 is an exploded view in side elevation of the injector mechanism per se.

FIG. 2 is an exploded view in side elevation of the injector mechanism, partially assembled, and a medicament ampule.

FIG. 3 is a longitudinal sectional view on an enlarged scale of the injector loaded with an ampule in position for use.

FIG. 4 is a section taken approximately on the line 4—4 of FIG. 3.

FIG. 5 is a longitudinal sectional view through the injector and contained ampule at the beginning of the operating stroke of the injector plunger.

FIG. 6 is a longitudinal sectional view of the device of FIG. 5 with the plunger and ampule parts in their position at the completion of the injection stroke.

FIG. 7 is a sectional detail of the injector trigger mechanism at the moment of release of the plunger.

FIG. 8 is an enlarged fragmentary view partially in section of a portion of the ampule plunger, the needle and needle guide.

The device includes an injector 10 having a cylindrical casing 12 with a threadedly detachable end cap 14. A cylindrical chamber 12 is adapted to removably receive a cylindrical medicament ampule 16. Rearwardly of the ampule chamber 12 is a bore 18 to receive a shank 20 of a plunger 22. An expansion coil spring 24 is interposed between the rear side of the plunger 22 and the rear end wall 26 of the injector 10.

The cylindrical ampule 16 has a reduced forward end 28 which has an open front end closed by a pierceable seal 30. In front of the seal 30 the end cap 14 is provided with an opening 32.

Within the cylindrical ampule 16 is a piston 34 of an elastomeric material and provided with a bore 36 in which is slidably received a tubular needle guide 38 within which is slidably carried a needle 40. The bore 36 terminates short of the front face of the piston 34 to provide a rupturable seal portion 42.

The needle 40 has a lumen 44 extending from its forward end rearwardly but is closed at its rear end by pinching the needle as at 46. The pinched portion 46 not only closes the rear end of the needle but provides a head portion to be contacted by the spring pressed plunger 22. It also serves as a stop when it engages the rear of the guide 38 to control the depth of penetration of the needle in the tissue of the user. This prevents the needle from being driven too far and interfering with proper flow of the liquid therethrough.

The needle 40 is provided with a liquid inlet port 48 at a longitudinal medial point on the needle. As viewed in FIG. 3, the initial position of the needle relative to its guide 38 and the piston 34 is such that the front end 50 of the needle lies near the front end of guide 38 and a short distance rearwardly of the sealed portion 42 of the piston. It should be noted that the liquid inlet port lies adjacent but enclosed by the rear portion of the guide 38 so that the lumen 44 is sealed from the interior of the ampule 16. It will also be seen that roughly half of the length of the needle is supported in the needle guide 38.

The injector 10 at its rearward portion is reduced as at 52 and upon this reduced portion is a cap 54 which is rotatable and longitudinally slidable upon the reduced portion 52. Rotational movement of the cap 54 is limited by a pin 56 in an arcuate slot 58 partially about the circumference of the reduced portion. The slot 58, at one end thereof, connects with a short longitudinal slot 60 as shown in FIGS. 4, 5, 6 and 7. Also, just forward of the cap 54 is a split ring 62 which lies above the reduced portion 52 and between a shoulder 64 and the front end of cap 54. The split ring 62 and the pin 56 provide a double locking means to prevent accidental movement of the cap 54 for a reason to be explained below.

The rearwardly extending plunger shank 20 is split to provide catch knobs 66 having forwardly facing shoulder surfaces 68 and rearwardly disposed cam surfaces 70. In the split portion is lodged a piece of elastomeric material 72 to bias the heads 66 away from each other.

The end closure 26 for the injector casing has an abutment surface 80 which faces rearwardly and engages the forwardly facing abutment surfaces 68 of the knobs 66 to hold the plunger shank 20 and the plunger in the position shown in FIG. 3 against the expansive action of the spring 24. As shown in FIG. 3 the inside of the cap 54 is provided with a recess 74 whose front edge 76 cams against the cam surfaces 70 to force the two heads 66 toward each other and out of engagement with the abutment surface 80 on the rear end portion 26 of the injector casing. However this can be done only after the split ring 62 is removed from in front of the cap 54 and the cap is turned counterclockwise from the position shown in FIG. 4 to align the pin 56 with the longitudinal slot portion 60.

When the plunger 22 is thus released and projected forwardly or to the left as viewed in the figures, the plunger will engage the pinched end 46 of the needle 40, causing it to move from the position of FIG. 3 to the position of FIG. 5. However as soon as the plunger hits the rear end of the needle, the forward end will be caused to pierce the sealing portion 42 of piston 34 and enter the medicament 78 in the ampule 16. Also at the time the plunger 22 reaches the position of FIG. 5 the fluid inlet port 48 will have left the cylindrical guide 36 and passed forwardly through the sealing portion 42 of the piston to enter the medicament 78. Thereupon continued movement of the plunger 22 will move the needle and its guide 38 forwardly until the plunger hits the rear face of piston 34, at which point the plunger guide and piston will all move forwardly until the forward face of the piston 34 engages the inside end portion of the ampule 16.

From the needle position of FIG. 5 until the needle has moved forwardly to pierce the end cap seal 30, the needle lumen 44 is not filled with liquid because there is equal liquid pressure at the tip of the needle and at the inlet port. However when the needle tip pierces the seal 30 and almost instantaneously penetrates the skin of the patient, the liquid pressure balance in the needle is broken and liquid will be forced through the inlet port 43, thence through the lumen 44 and out of the end of the needle during the movement of the end of the needle into the tissue of the patient. Thus a considerable percentage of the liquid medicament 78 is distributed in the tissue throughout the path of movement of the needle so that there is no large concentration of liquid pressure after the needle has penetrated to its predetermined depth.

It will be seen that I have provided a hypodermic module which has the advantage of the gradual liquid medicament dissipation during the travel of the needle point into the tissue as in Schmitz U.S. Pat. No. 4,194,505, but with the additional important feature that the self-contained medicament and needle module is such that the needle is not immersed in the medicament until the moment of injection. This is highly important in situations where the medicament is corrosive in nature and would corrode and render ineffective the needle which is maintained in an immersed condition, and more importantly contaminate the liquid medicament.

It should of course be understood that various changes can be made in the form, details, arrangement and proportions of the various parts without departing from the spirit of the invention.

What is claimed is:

1. A corrosive protected hypodermic module comprising:
   a cylindrical barrel open at its forward end,
   a pierceable seal across said forward end of said barrel,
   a piston in said barrel in slidable sealed relation to the interior wall of the barrel,
   said barrel, between said pierceable seal and said piston defining a medicament chamber,
   said piston having a longitudinal bore therein,
   a pierceable diaphragm across the forward end of said bore, sealing the bore from said medicament chamber,
   and a tissue piercing needle supported in said bore behind the pierceable diaphragm and longitudinally slidable in said bore.

2. The structure in claim 1, and a needle guide slidably mounted in said bore,
   and said tissue piercing needle being slidably mounted in said guide and extending rearwardly therefrom.

3. The structure in claim 2, and said guide extending rearwardly from said bore and the rear of said piston,
   and said needle having its forward end in the forward end of said guide adjacent the rear of said pierceable diaphragm.

4. The structure in claim 3, and said needle guide being tubular,
   and the rear end of said needle having a transverse dimension greater than the inner diameter of said tubular needle guide.

5. The structure in claim 3, and said needle guide being tubular and receiving said needle therein,
   and said needle being of greater length than that of said guide to project said needle a greater distance forwardly than said tubular guide when the needle and guide are moved forwardly relative to said piston.

6. The structure in claim 4, and said needle guide having a greater resistance to sliding movement in said piston bore than that of said needle relative to said guide.

7. The structure in claim 3, and said needle extending rearwardly from said guide,
   said cylindrical barrel having an open rear end, an injector comprising a housing with a chamber receiving said cylindrical barrel and having an open forward end,
   said injector having a spring loaded plunger therein movable from a position adjacent the rear end of said cylindrical barrel to a position forwardly in said barrel,
   and a trigger device in operative association with said spring loaded plunger to release the plunger and permit it to be propelled forwardly in said cylindrical barrel.

8. The structure in claim 7, and said injector having a plunger compartment therein rearwardly of said chamber for said cylindrical barrel, said plunger being slidable in said compartment toward and away from said cylindrical barrel, a spring device positioned between a portion of said injector and said plunger to propel said plunger forwardly, and said trigger releasably restraining said plunger against the action of said spring device.

9. The structure in claim 8, and said injector having one of a catch and a catch retainer on a portion thereof, said piston having the other of said catch and catch retainer thereon, said catch being positioned to engage said catch retainer and hold said plunger against the action of said spring device, and a trigger element carried by said injector and movable relative thereto to disengage said catch from said catch retainer.

10. The structure in claim 9, and said catch comprising a laterally resilient head on the rear of said plunger and having a forwardly facing abutment surface, said catch retainer comprising a relatively stationary portion of said injector having a rearwardly facing abutment surface engageable by the forwardly facing abutment surface of said head, and a trigger element carried by said injector and movable into engagement with said resiliently mounted head to displace its abutment surface from that of said relatively stationary portion of said injector.

11. The structure in claim 10, and said trigger device including a cap mounted on the rear end of the trigger device and being movable about and longitudinally of the remainder of the injector, and means for locking said cap against longitudinal movement in one of the rotational positions of the cap.

12. The structure in claim 11, and additional locking means for said cap removably mounted on said injector and blocking said cap against longitudinal movement regardless of the rotational position of the cap.

13. The structure in claim 6, and said needle having a longitudinal lumem therein from the forward end thereof and terminating short of the rear end thereof and having a liquid in that port in flow communication with said lumen rearwardly of the forward end of the lumen.

14. The structure in claim 13, and said needle, in a rearward position relative to said guide, having its inlet port lying within said tubular guide adjacent the rear end thereof.

15. The structure in claim 14, and said needle, in a forward position thereof relative to said guide, being extended through said pierceable diaphragm, and said inlet port being located forwardly of said diaphragm and the forward end of said needle guide.

16. The structure of claim 1, and a tubular needle guide slidably mounted in said bore, said needle guide, at its rear end, having a lateral projection greater than the bore in said piston.

17. The structure in claim 16, and said lateral projection comprising a radial flange.

18. The structure in claim 16, and the rear end of said needle having a transverse dimension greater than the inner diameter of said tubular needle guide.

* * * * *